(12) United States Patent
Tudor

(10) Patent No.: US 7,069,776 B2
(45) Date of Patent: Jul. 4, 2006

(54) METHOD FOR MEASURING PARTICLE CONCENTRATION DURING INJECTION PUMPING OPERATIONS

(75) Inventor: Robin Tudor, Black Diamond (CA)

(73) Assignee: ILI Technologies,Corp., Calgary (CA)

( * ) Notice: Subject to any disclaimer, the term of this patent is extended or adjusted under 35 U.S.C. 154(b) by 0 days.

(21) Appl. No.: 10/616,142

(22) Filed: Jul. 8, 2003

(65) Prior Publication Data

US 2004/0007059 A1 Jan. 15, 2004

(30) Foreign Application Priority Data

Jul. 9, 2002 (CA) ................................. 2,3920,737

(51) Int. Cl.
*E21B 49/08* (2006.01)
*G01N 29/02* (2006.01)

(52) U.S. Cl. ................................. 73/152.42; 73/152.32; 73/61.75

(58) Field of Classification Search ............. 73/152.32, 73/152.42, 61.75

See application file for complete search history.

(56) References Cited

U.S. PATENT DOCUMENTS

| | | | |
|---|---|---|---|
| 3,906,780 A * | 9/1975 | Baldwin | ..................... 73/61.75 |
| 5,390,547 A | 2/1995 | Liu | |
| 5,441,340 A * | 8/1995 | Cedillo et al. | .................. 366/2 |
| 5,741,980 A | 4/1998 | Hill et al. | |
| 6,118,104 A * | 9/2000 | Berkcan et al. | ............. 219/494 |
| 6,354,147 B1 | 3/2002 | Gysling et al. | |
| 6,381,549 B1 | 4/2002 | Smith | |

\* cited by examiner

*Primary Examiner*—Daniel S. Larkin
(74) *Attorney, Agent, or Firm*—Lerner, David, Littenberg, Krumholz & Mentlik, LLP

(57) ABSTRACT

In a well bore operation in which a particulate is added to a fluid stream, a method of determining the concentration of said particulate in said fluid stream comprising the steps of measuring the rate of flow of the fluid stream, determining the rate of particulate flow in the fluid stream using an acoustic sensor and calculating the concentration of particulate in the fluid stream using results from the measuring and determining steps.

18 Claims, 10 Drawing Sheets

METHOD FOR MEASURING PARTICLE CONCENTRATION DURING INJECTION PUMPING OPERATIONS

FIELD OF THE INVENTION

The present invention relates to a method of quantifying the concentration by mass or volume of a particulate of known size and density that has been added to a fluid stream of known density, rate and viscosity.

BACKGROUND OF THE INVENTION

The pumping services sector within the oil and gas industry injects fluid into wells to stimulate production or to encase well bore tubulars. The fluids that are pumped usually include various chemicals and solid particulates. The chemicals are added to enhance the properties of the fluids or to make them more compatible with the hydrocarbon bearing formation. The particulates that are added to the fluids are used as propping agents, diverting agents, or as extenders that reduce volumetric cost, change volumetric density, or even enhance properties of the base fluid.

Sands (silicon, ceramic, resin), glass beads, and salts are examples of particulates that are added to fracture fluids, acids, and cements. All of these products come in defined densities and size ranges. The operations that employ these materials are pre-engineered for varying concentrations during the treatment dependent on the desired final results.

Within the industry, it is desirable to monitor the quality of the fluid within the system. This includes monitoring the concentration of particulates within the fluid. Current methods for quality control of the addition of particulates includes: batch weighing, both pre and post job, mechanical metering during the addition of the particulates, or radioactive density measurements of the fluid slurries during operations.

Batch weighing provides quality control of the cumulative total product used, but does not provide quality control during on the fly operations for pre-engineered programs that vary the rate at which particulates are added during different phases of the injection.

Mechanical metering involves measuring the rate at which the particulate is added and the rate of the fluid prior to addition (clean rate) and then using these rates to calculate the particulate concentration in the slurry. The calculation for concentration is based on the knowledge of the density of both the fluid and particulate. However, mechanical metering is prone to slippage and inaccuracies due to the efficiencies of the mechanical system being employed. The quality of the measurement is therefore limited.

Another method of measuring concentration is the use of radioactive densitometers. The densitometer measures the absolute density of the slurry flowing in the pipe, and then from knowledge of the fluid density and the particulate density, the particulate concentration can be calculated.

Radioactive density measurements are the most accurate method of concentration measurements. The densities of the fluids and particulates are known prior to pumping and the radioactive density meter reads the absolute density of the slurry from which the particulate concentration can be calculated. The problem with radioactive density meters is the relative cost, management of the radioactive source, and the limitations of the meter. The limitations of the radioactive meter are its accuracy at low densities and its sensitivity when the differential density of the carrying fluid and the particulate is small.

An alternative solution taught in U.S. Pat. No. 5,390,547 to Liu is a method of splitting the phases in the fluid apart in order to calculate concentration. In Liu, the phases are split into gas/fluid or gas/free water/oil-water emulsions and the rates are individually measured. However, the solution in Liu is not practical for the measurement of particulate concentration due to the high pressures seen during injection operations.

Other solutions include a system of multiple acoustic sensors tied together via fiber optics as described in U.S. Pat. No. 6,354,147 to Gysling et al. However, the use of multiple sensors prohibitive and the system taught by Gysling is difficult to operate in the extreme mobile environment of oil field pumping operations.

A further solution includes a system that uses a transmit and receive process. U.S. Pat. No. 6,381,549 to Smith teaches a system in which a wave is transmitted, and the "echo" and transmit time is used to determine the rate and density. This system will again however be subject to high costs due to the need for multiple sensors (both transmit and receive sensors) and will again be negatively affected by the harsh mobile environment.

Other systems, including the systems taught in U.S. Pat. No. 5,741,980 to Hill et al., are also complex, making them cost ineffective and highly vulnerable to the harsh operational environment of the field.

SUMMARY OF THE INVENTION

The present invention seeks to overcome the deficiencies of the prior art by providing a method for quality control for the injection of particulates into a fluid stream. The present invention utilizes an acoustic sensor affixed to the outside of a pipe through which the combined fluid and particulate flow. The invention further utilizes a flow rate sensor to determine the flow rate of the clean fluid or the slurry. The method further includes a means of combining the flow rate and the particulate flow rate to calculate and display particulate concentration by volume or mass.

According to an aspect of the present invention, there is provided in a well bore operation in which a particulate is added to a fluid stream, a method of determining the concentration of said particulate in said fluid stream comprising the steps of measuring the rate of flow of said fluid stream; determining the rate of particulate flow in said fluid stream using an acoustic sensor; and calculating the concentration of particulate in said fluid stream using results from said measuring and determining steps.

According to another aspect of the invention, there is provided a fluid conveying operation having a fluid line for carrying a fluid mixed with a particulate, an apparatus for measuring the concentration of the particulate in the fluid comprising a fluid flow meter located within the fluid line for measuring the rate of the fluid; an acoustic sensor located outside the fluid line near a bend in the fluid line for measuring the rate of particulate flow; and a calculating means for determining the concentration of the particulate using data from said fluid flow meter and said acoustic sensor.

According to a further aspect of the invention, there is provided in a well bore operation having a clean fluid line leading to a blender, the blender mixing a particulate with a clean fluid to create a slurry, a slurry line from said blender to a high pressure pump, the high pressure pump pumping the slurry to a wellhead using a high pressure line, a system for measuring the concentration of the particulate within the fluid comprising a fluid flow meter affixed within the clean fluid line for measuring the rate of fluid flowing; an acoustic sensor affixed to the exterior of the high pressure line at a bend in the high pressure line, the acoustic sensor measuring the rate of particulate flow; and a calculating means for calculating the concentration of particulate using data from said fluid flow meter and said acoustic sensor.

BRIEF DESCRIPTION OF THE DRAWINGS

For a more complete understanding of the nature and objects of the invention, reference should be had to the following detailed description taken in connection with the accompanying drawings in which.

DETAILED DESCRIPTION OF THE DRAWINGS

Figure 1:
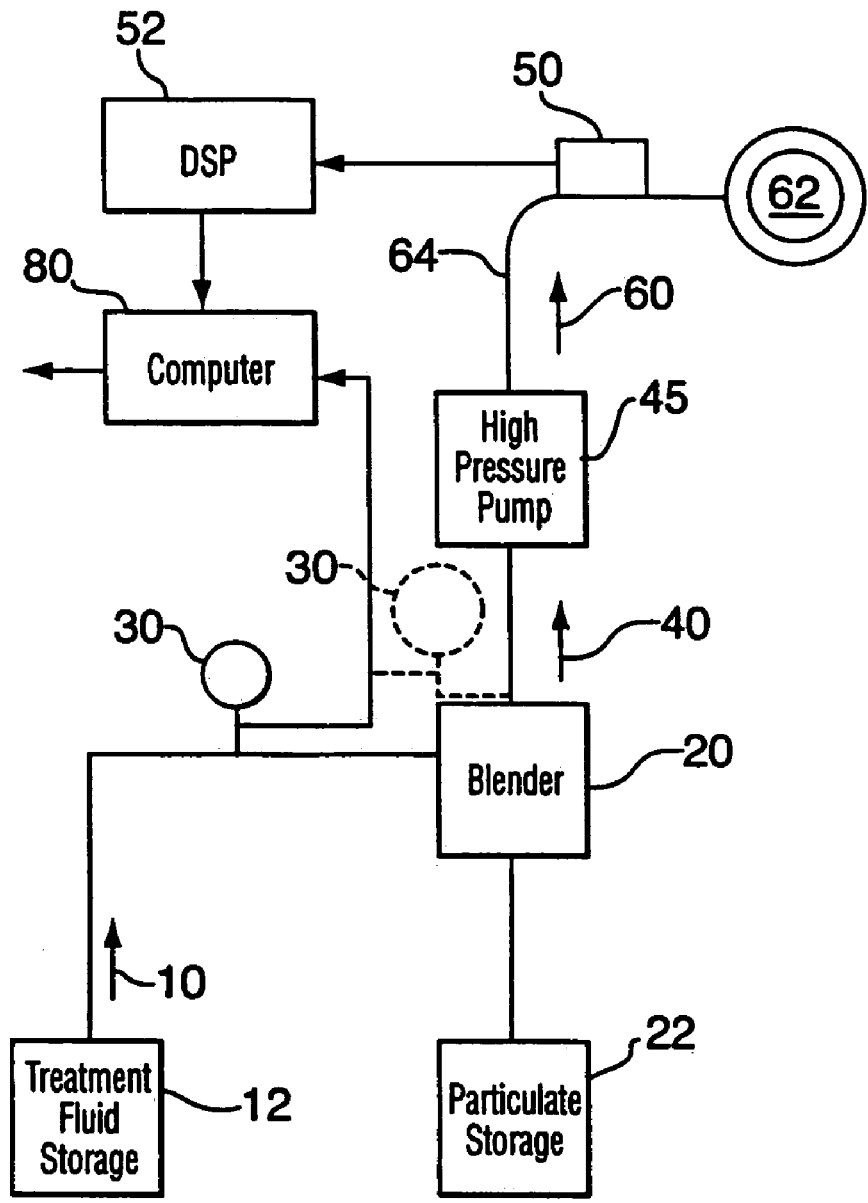
FIG. 1 is a schematical diagram of the placement of the sensors within a fluid pumping system for injecting pressurized slurries into a well bore.

Reference is made to FIG. 1. The applicant has found that through the addition of two sensors to a pumping operation, along with the means to process data, an accurate, robust and cost-effective method of measuring the concentration of particulates in a fluid can be achieved. FIG. 1 schematically illustrates the location of the sensors in the present system.

FIG. 1 shows the basic arrangement of equipment for an oil field pumping services operation 1. Clean treatment fluid 10, which is released from high pressure pump fluid storage 12, is brought to an operational location separately from the particulates which are stored in particulate storage 22. Conventional blender equipment 20 is used to add chemicals and particulates to clean fluid 10 to create the required slurry 40. The blender equipment combines the fluid and particulates and then pumps the mixture to a high pressure pumper 45. High pressure pump 45 pressurises the slurry into a high pressure slurry 60 and pumps it to the well head 62 using high pressure rated tubulars 64 such as high pressure rated pipe for injection into the well bore.

The applicant has found that by adding a fluid flow meter 30 and an acoustic sensor 50 to the system, data can be obtained which can be used to calculate the concentration of the particulates in the fluid. In a preferred embodiment, a fluid flow meter 30 is added between fluid storage 12 and blender 20, and therefore before particulate is added to the fluid. This ensures flow meter 30 measures clean fluid, and is not affected by particulates within the fluid.

Alternatively, it is envisioned that a slurry flow meter found along the line carrying low pressure slurry 40 can be used as shown in FIG. 1 in broken lines. However, due to the particulates within the slurry, these meters can be inaccurate, and tend not to last very long in any event, and therefore it is preferred to measure the clean fluid flow rate.

Figure 2:
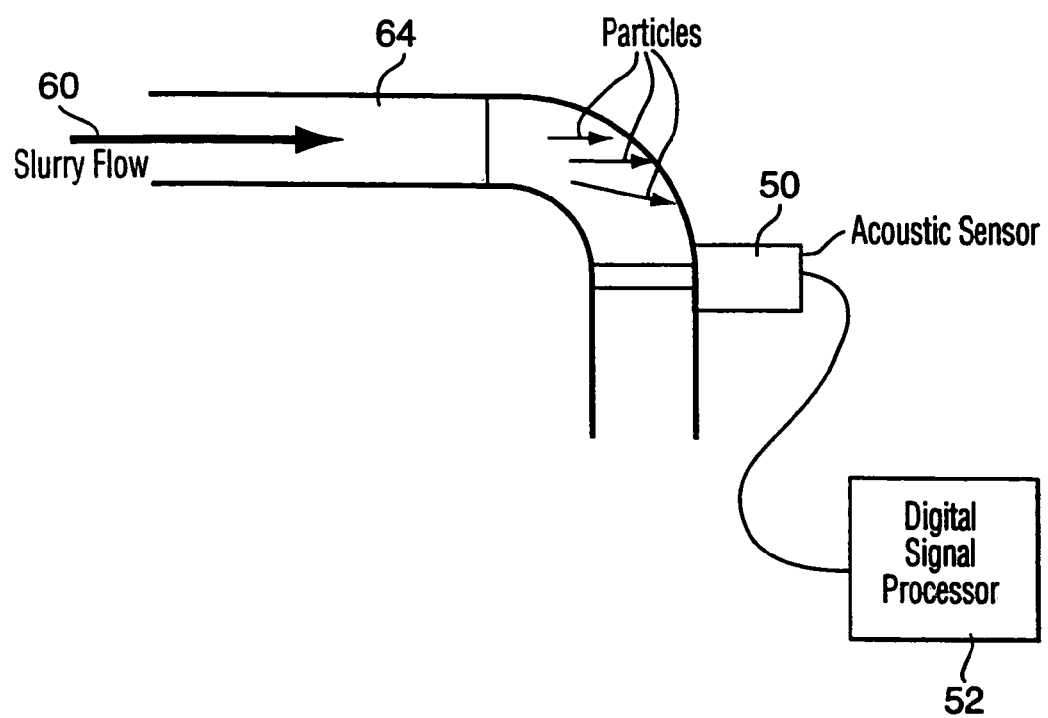
FIG. 2 is a schematical diagram of a high pressure slurry flow pipe with an acoustic sensor affixed thereto.

Reference is now made to FIG. 2. Acoustic sensor 50 is added to the outside of high pressure pipe 64 delivering slurry 60 to the well head. The sensor is preferably mounted on the downstream side of a 90° in the pipe, however, it can also be located downstream of a smaller degree bend.

In operation, particulates will hit the inside wall of pipe 64 as the slurry 60 flows around the corner, creating noise within a certain range of frequencies that will be detected by acoustic sensor 50. This is due to the inertial effect on the particles as the fluid moves around the corner. The particles striking the pipe will initiate an acoustic wave in the pipe and that will be measured by sensor 50. The amplitude of the output from the sensor has been found to be proportional to the amount of particulate flowing through the pipe. More specifically, the output from sensor 50 will rise and fall in response to the amount of noise produced by the particles hitting the pipe's inner wall. The amplitude of the noise reflects the energy of the particles as they hit. It is believed that sensor 50 records the kinetic energy (as determined by the formula $E=\frac{1}{2}mv^2$, where m is the mass of the particle and v is its velocity) in the frequency range that sand and similar particulates release when they hit the metallic inner wall of pipe 64. The greater the number of hits, the greater the amount of energy transferred to the pipe and detected by sensor 50 whose output will rise and fall accordingly in response. As will be appreciated, higher viscosity treatment fluids will reduce the number of hits and their amplitude and hence, as will be discussed below, the effect of viscosity is factored into the present system to adjust for a more accurate result.

In operation, it has been found that acoustic sensor 50 is indiscriminate in its measurement of ultrasonic waves within the metal of the treatment pipe. This means that sensor 50 measures the noise of, for example, waves created by the fluid, by mechanical motions from the high pressure pumps, and from any other sources inducing acoustic waves in the metal. As illustrated in FIGS. 1 and 2, a digital signal processor 52, which is integrated into the sensor by some manufacturers, is used to remove all unwanted noise and focus on the frequency of the acoustic waves created by the particulates. The removal of extraneous noise detected using these types of sensors is known and one skilled in the art will appreciate various methods for filtering noise and such techniques accordingly need not be described in detail herein.

Acoustic sensors 50 are known in the art, and examples of suitable acoustic sensors include the ClampOn™ DSP particle monitor and sensors produced by Roxar™. These acoustic sensor systems have previously been utilized in oil field operations to measure particulate mass volume in fluids produced from well bores. These values are used for the prediction of corrosion, abrasion and adjustment of production to minimize particulate production, but are measured independently of fluid or slurry flow rates. This is due to the fact that the properties of the produced fluids, including density, viscosity and gas content are all unknown, making accurate computation all but impossible. Hence, acoustic techniques have not in the past been used in the area of quality control for injected fluids.

Further, it has been previously thought that the use of acoustic sensors for the purposes described herein was not viable because it was believed that the high concentration of particulates utilized in the types of high pressure, large volume pumping operations described herein would make the system unworkable.

The electronic signals from fluid flow meter 30 and acoustic sensor 50 are processed, preferably on a continuous basis, using a computer 80. Within computer 80, software allows the input of the known fluid parameters of composition, density, viscosity, velocity, aeration and any other parameter that may affect the amount and amplitude of noise transmitted to the acoustic sensor by the fluid as it flows around the bend in pipe 64. There will be similar inputs for the known particulate parameters of density, size, velocity and any other parameters that may affect the amount and amplitude of noise produced by the particulates as they impinge on the pipe's inner wall. When pumping down a well bore for treatment or other purposes, these parameters and variables will all be known, which facilitates the use of acoustics for the quality control of injected slurries.

Signal conditioning parameters for the fluid flow meter and acoustic sensor will also be input into computer 80. These include the parameters required to convert raw signals into engineering units.

The filtered signals from digital signal processor 52 and from clean fluid flow meter 30 are input into computer 80. Computer 80 is programmed to perform the following calculations:

$$\text{Flow Rate} = \frac{\text{Flow Meter Raw Output}}{\text{Input Pulses per Unit}} \quad (1)$$

Where Flow Rate refers to the rate of either the clean fluid or the slurry, expressed as units of volume per unit of time;

Where Flow Meter Raw Output is the output signal from flow meter 30; and

Where Input Pulses per Unit is a variable entered into computer 80 to convert the raw signal from flow meter 30 to fluid flow expressed in engineering units (eg. 1/min). In a preferred embodiment, flow meter 30 is a turbine wheel that spins when fluid moves through it. Magnetic sensors detect the number of revolutions, and the Input Pulses per Unit is used to convert the number of rotations to an engineering unit such as kilograms, pounds, gallons, or cubic meters. The IPU will normally be supplied by the flow meter's manufacturer.

$$\text{Particulate Rate} = \left[ \frac{(\text{Digital Signal Raw Output}(DSRO) - \text{Amplitude Offset})}{\text{Amplitude Increment per Unit}(AIU)} \right]^{Exp} \quad (2)$$

Where Particulate Rate is expressed as units of mass per unit of time;

Where Digital Signal Raw Output is the raw output signal from digital signal processor 52 representing the measured energy in the frequency range of the particulates hitting the pipe's inner wall. The sensor converts the measurement into an electrical signal and then converts the amplitude of that signal into a digital number which, for the sensor used by the applicant for testing purposes, will vary between 0 and 5,000,000. This number will be the DSRO;

Where the Amplitude Offset is the digital number from sensor 52 representative of the noise level in pipe 64 without particulate in the fluid stream. The offset will vary depending upon the type of sensor used, the type of pipe the sensor is attached to and the characteristics of the treatment fluid (eg. velocity, viscosity, composition). In tests performed by the applicant, the amplitude offset has been in the 5,000 to 11,000 range;

Where the Amplitude Increment per Unit is another variable entered into computer 80 to convert the DSRO from sensor 52 into a particulate rate expressed in engineering units meaningful to the system's operator, eg. kg/min. The AIU will vary depending upon the type of pipe, the type of fluid and particulate and the other factors referred to above including velocity and viscosity. In tests performed by the applicant, the AIU will vary in the range of 8,500 to 25,000, although numbers outside this range are contemplated as additional tests are performed using different pipes, fluids, particulates and sensors to obtain values for the AIU representing the different combinations of these elements likely to be encountered in the field; and Where Exp is an exponent that is another variable entered into computer 80 to covert the raw signals from acoustic sensor 50 into the Particulate Rate expressed in engineering units of mass/time. An exponent is used to account for possible non-linearity in sensor 50 and in tests performed by the applicant a range of Exp from 0.9 to 1.35 has been used, although values outside this range are contemplated. The sensor manufactures will typically provide the Exp to be used depending upon particle concentration and fluid viscosity but specify that an Exp of 1 can be used in most cases, which takes this variable out of the equation.

$$\text{Concentration} = \frac{\text{Particulate Rate}}{\left[ \text{Clean Fluid Rate} + \frac{\text{Particulate Rate}}{\text{Particulate Density}} \right]} \quad (3)$$

Where Concentration is the concentration of particulates in the slurry expressed in units per volume of slurry;

Where Particulate Rate is the result from equation (2);

Where Clean Fluid Rate is the result from equation (1) when the flow meter measures flow before the particulate has been added to the stream; and Where Particulate Density is the density of the particulates added to the stream expressed as units of mass per units of volume (eg. kg/m$^3$)

OR $$\text{Concentration} = \frac{\text{Particulate Rate}}{\text{Slurry Flow Rate}} \quad (4)$$

Where Concentration is the concentration of particulates in the slurry expressed in units of mass per volume;

Where Particulate Rate is the result from equation (2); and

Where Slurry Flow Rate is the result from equation (1) when the flow meter measures flow after particulates have been added to the stream.

As these formulas show, the flow rate is proportional to the raw output from the flow meter, and is inversely proportional to the input pulses per unit.

The particulate rate is found by taking the digital signal raw output sensor 50 and subtracting the amplitude offset. Then is then divided by the amplitude increment per unit.

Particulate concentration can be calculated by dividing the particulate rate by a combination of the clean fluid rate and the particular rate divided by the particulate density.

Figure 3:
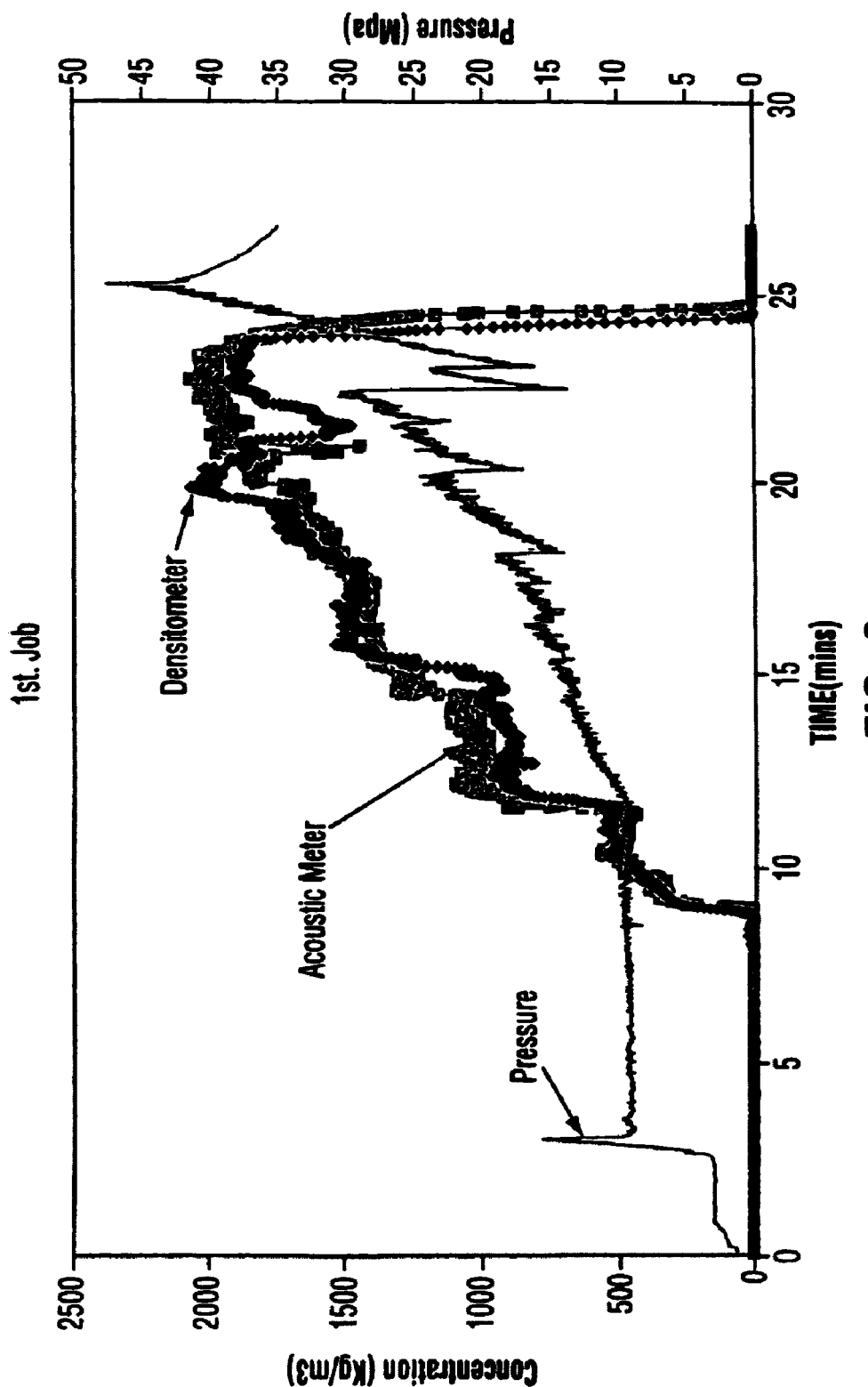
FIG. 3 is a graph of a first test in which the particulate concentration attained using the present method is compared with the results of a radioactive densitometer and in which the pressure is superimposed.

FIG. 3 shows a graph which compares particulate concentrations found using the present acoustic method with those found using a radioactive densitometer. The radioactive densitometer has been found to be an accurate means to calculate concentration, and is therefore used as a baseline reference. FIG. 3 additionally shows the pressure of high pressure slurry 60 in order to demonstrate how this pressure affects the results.

Figure 4:
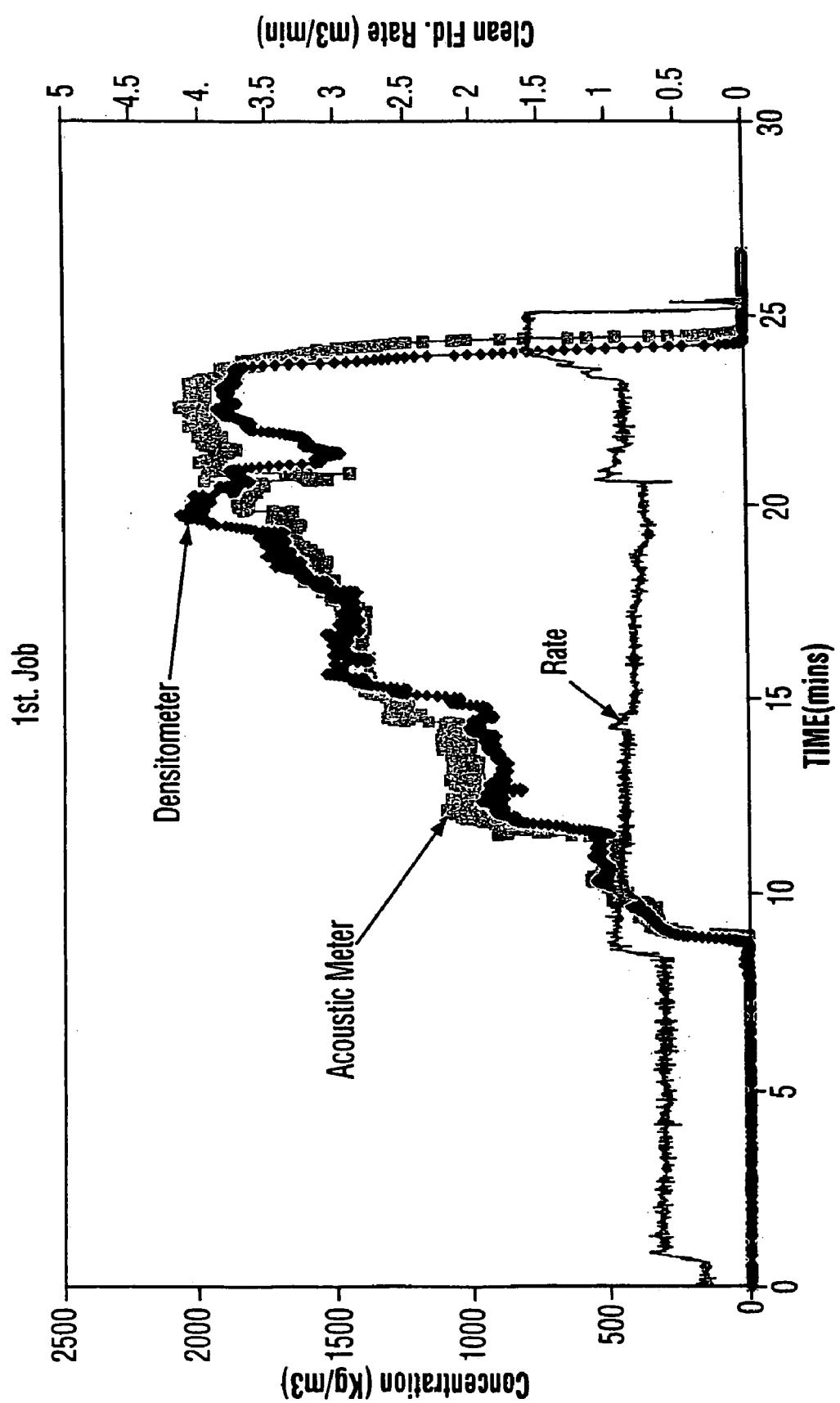
FIG. 4 is a graph which includes the concentration comparison of FIG. 3 and further shows the clean fluid rate measurements.

FIG. 4 is a graph of the same concentration measurements as in FIG. 3, but has substituted the pressure measurements with the clean fluid flow rate in order to demonstrate how changes in the rate of flow of clean fluid affects the concentration measurements using the method of the present invention.

Figure 5:
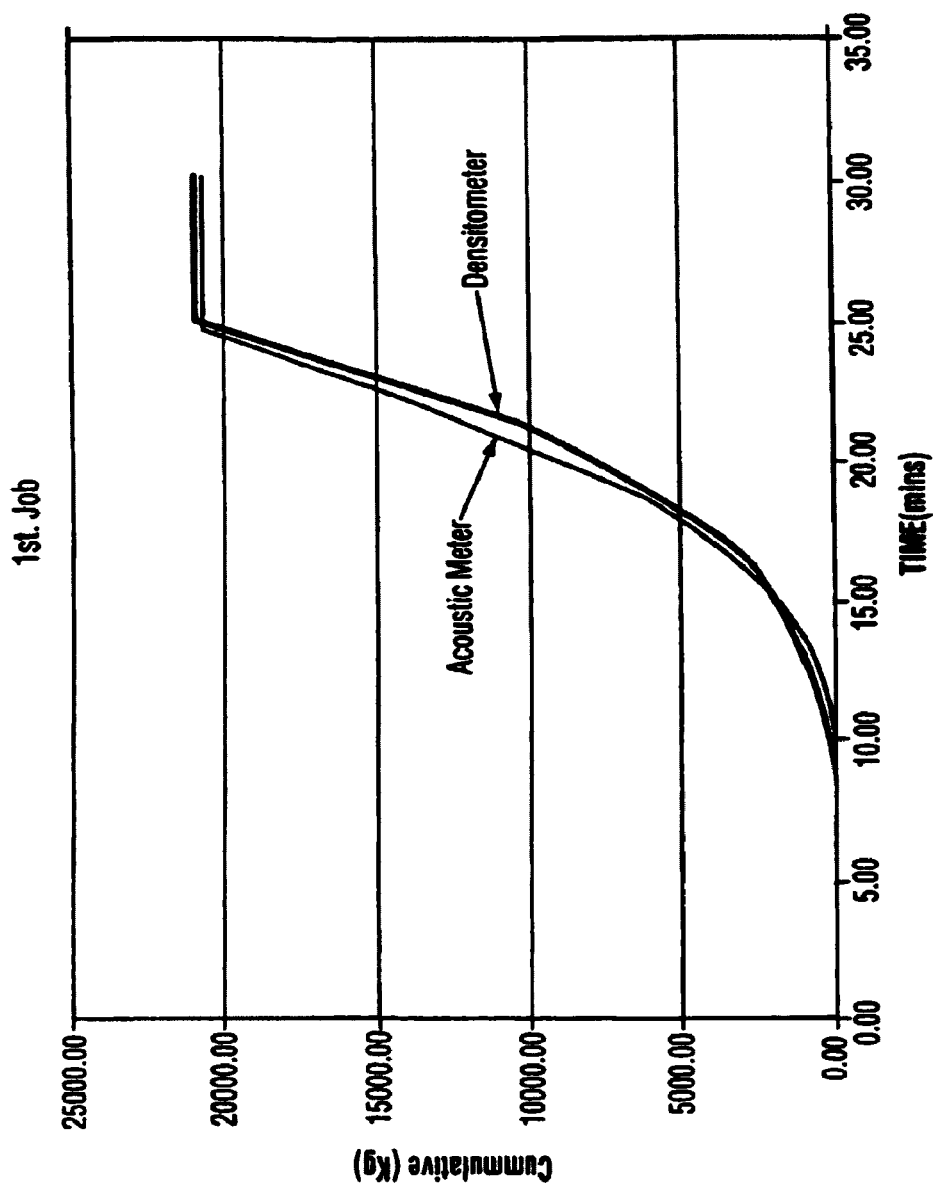
FIG. 5 is a graph of a comparison of the cumulative mass as detected by the clamp-on acoustic tool versus the densitometer.

FIG. 5 shows the cumulative mass of particulate added to the treatment fluid in the course of the entire job measured by both the acoustic sensor and the densitomer.

Figure 6:
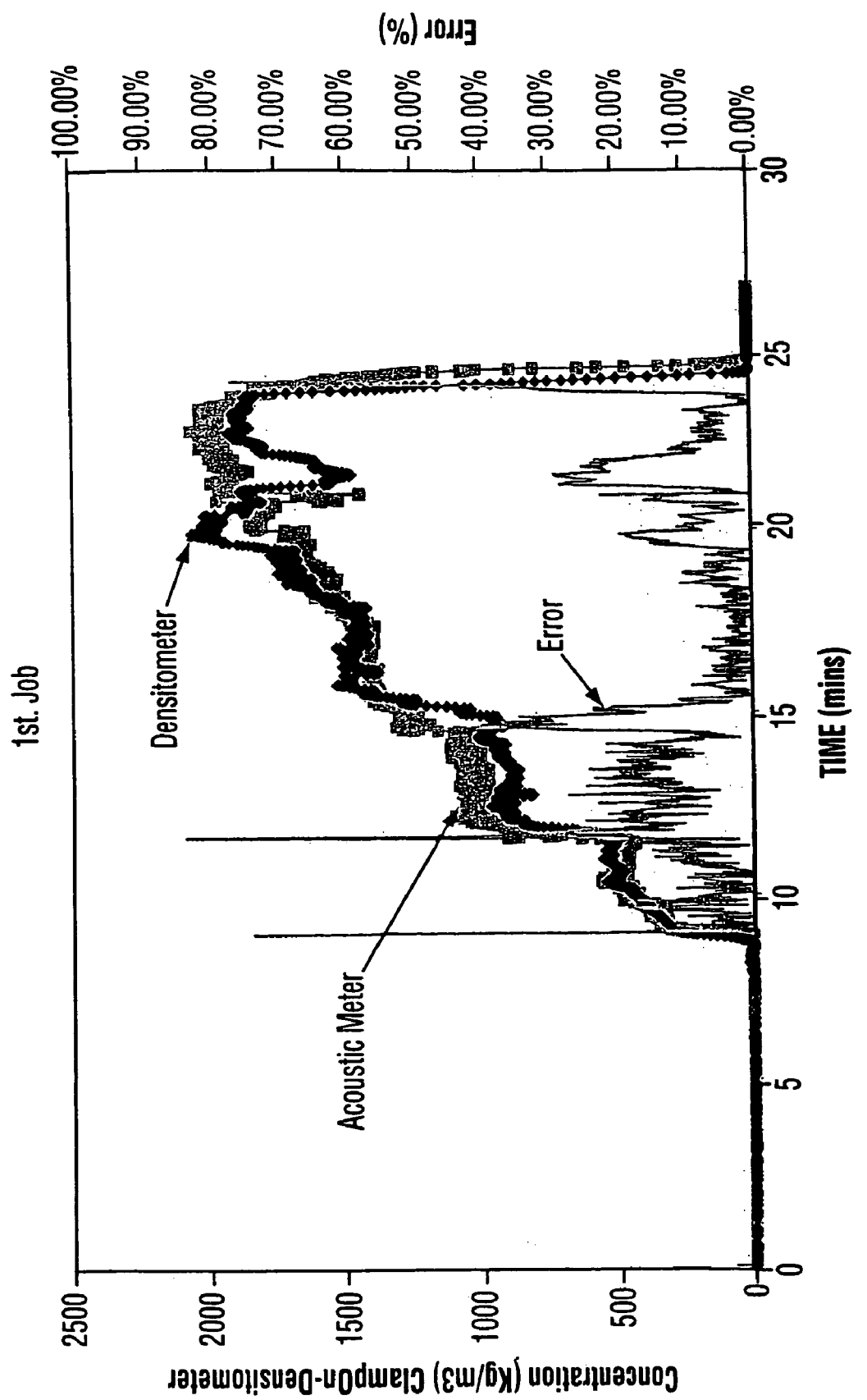
FIG. 6 is a graph showing the comparison between particulate concentrations obtained using the clamp-on acoustic sensor and the densitometer as shown in FIG. 3, along with a depiction of the percent error.

FIG. 6 shows the percentage error in concentration as measured between the base radioactive densitometer, and that measured by the acoustic method of the present invention. The results show that the absolute percentage of error compared with the radioactive density meter was a maximum of 50% with an average less than 20% and the cumulative mass volume error being less than 1%.

Figure 7:
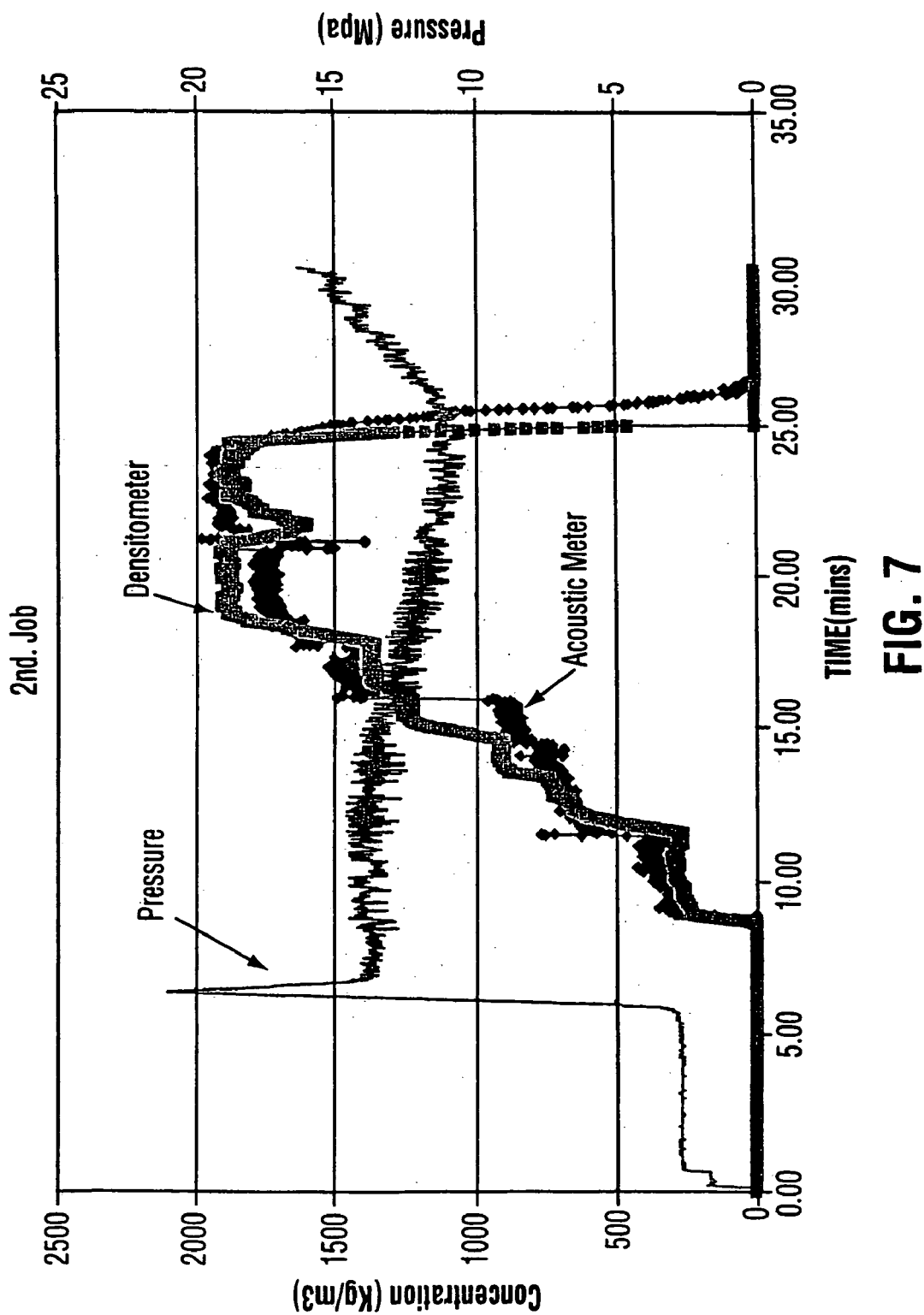
FIG. 7 is a graph showing the results of a second test in which the concentration attained using the present method is compared with the results of a radioactive densitometer and in which the pressure is superimposed.

FIG. 7 graphs a second test in which a radioactive densitometer is again used as the base, for comparison to the results obtained by the present method using an acoustic sensor. FIG. 7, like FIG. 3, also charts the pressure of high pressure slurry 60.

Figure 8:
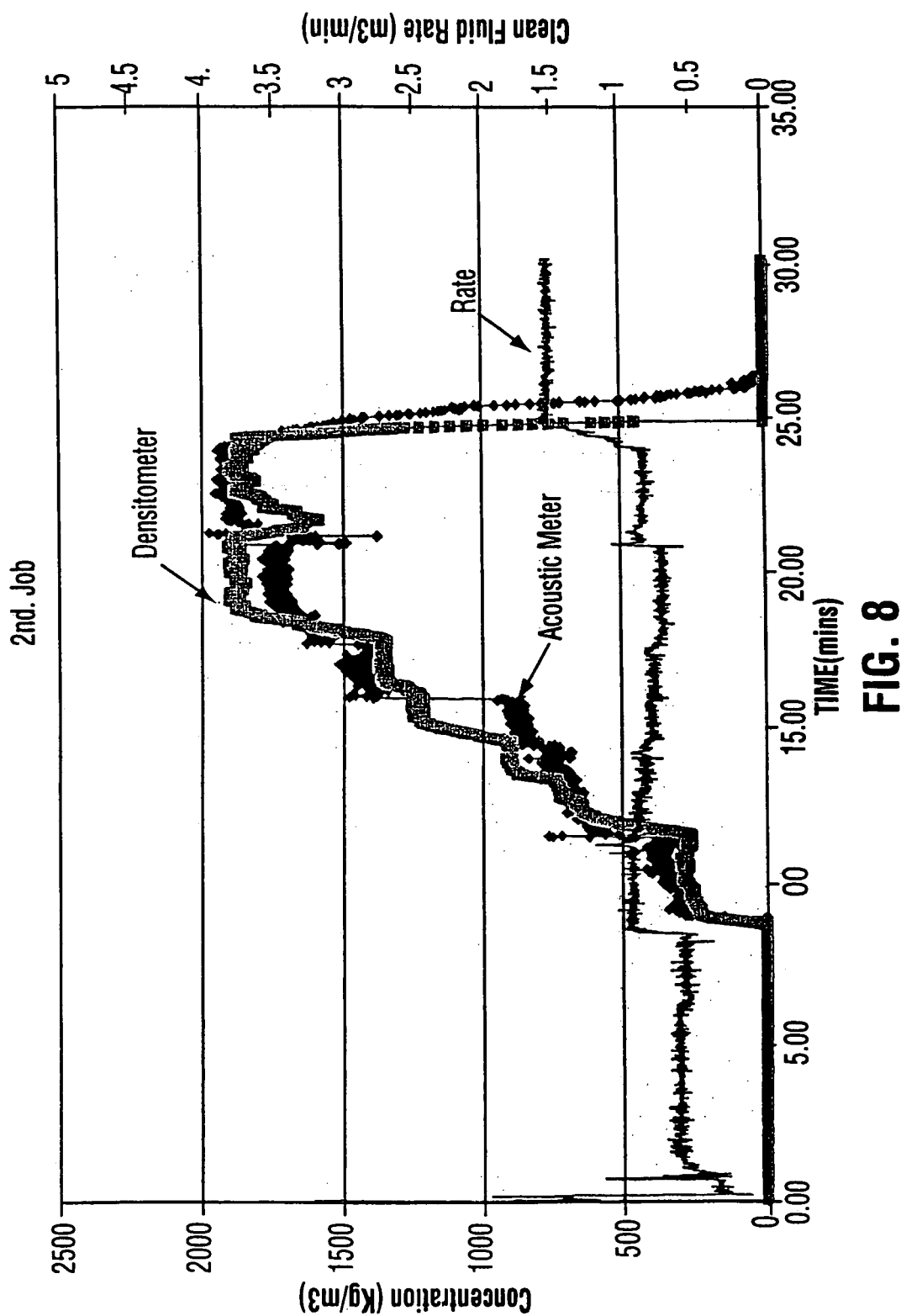
FIG. 8 is a graph of the concentration comparison of FIG. 7 and which further charts the clean fluid rate measurements.

FIG. 8, like FIG. 4, shows the clean fluid flow rate and its effects on the readings by the method of the present invention as compared with a radioactive densitometer.

Figure 9:
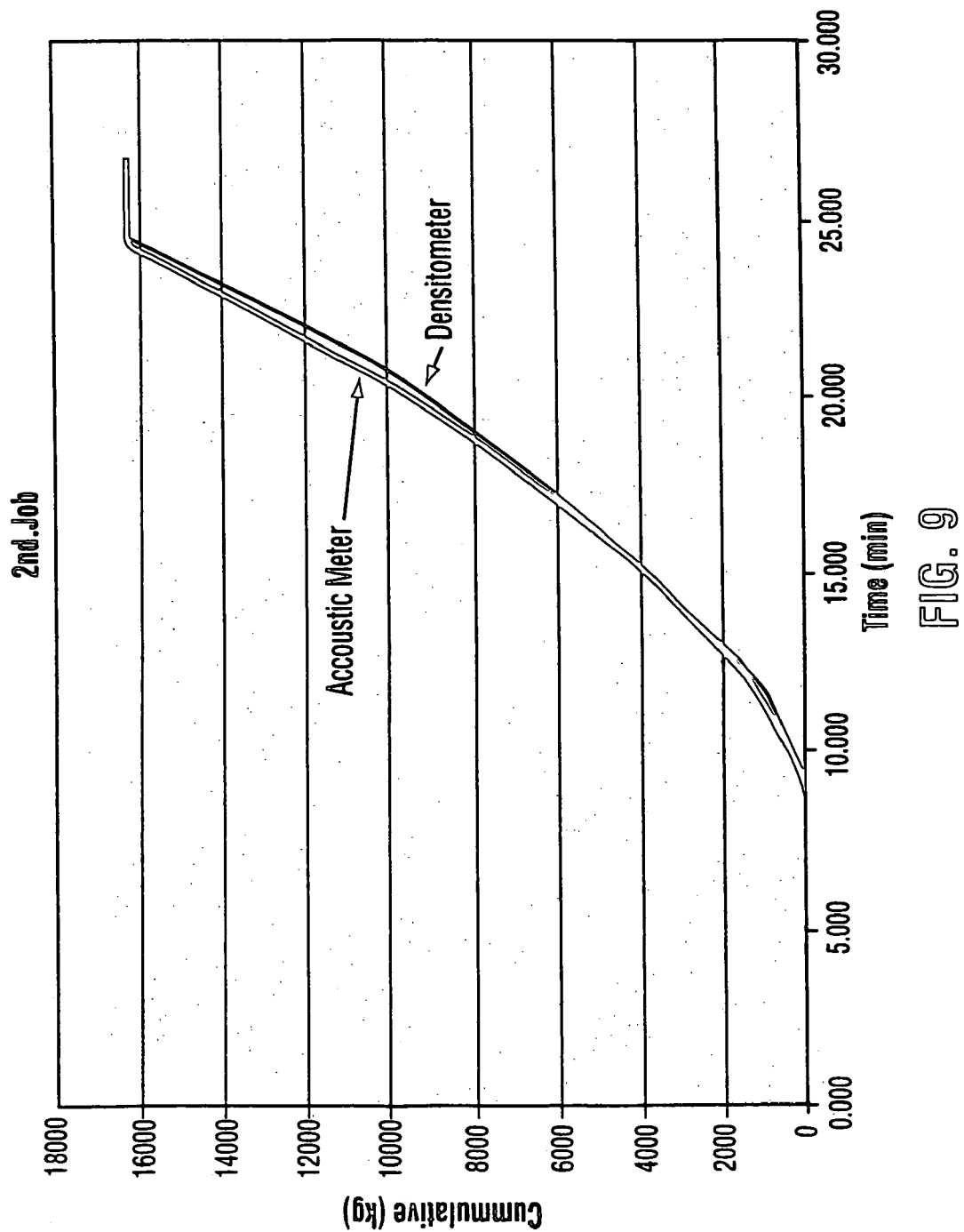
FIG. 9 is a graph of a comparison of the cumulative mass as detected by the clamp-on acoustic tool versus the densitometer.

FIG. 9 shows the cumulative mass readings using the densitometer and the method of the present invention.

Figure 10:
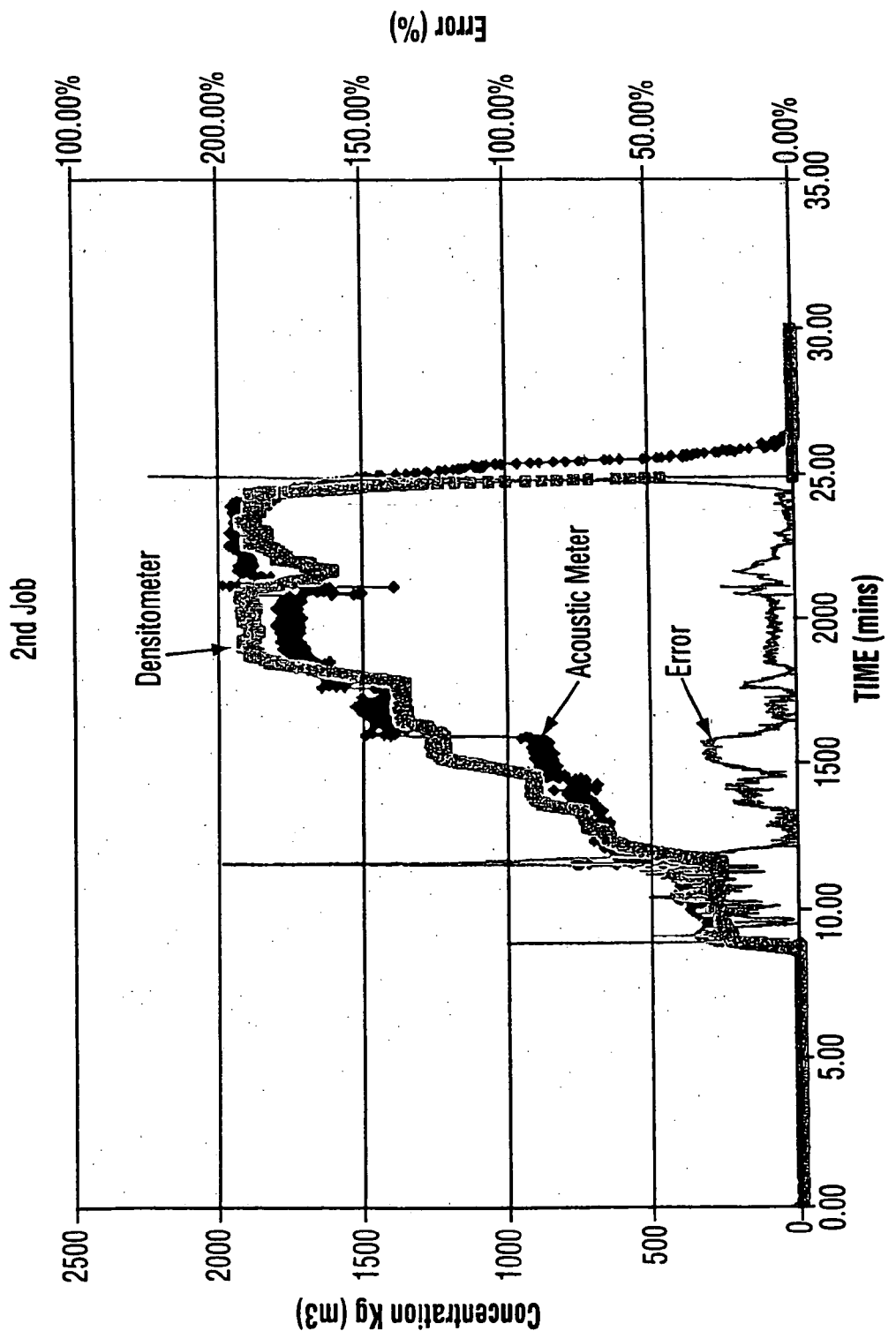
FIG. 10 is a graph showing the comparison between particulate concentrations obtained using the clamp-on acoustic sensor and the densitometer as shown in FIG. 7, along with a depiction of the percent error.

FIG. 10 shows the absolute error of the second test between the densitometer as the base and the acoustic method of the present invention. As indicated above, the results show that the absolute percentage of error compared with the radioactive density meter was a maximum of 50% with an average less than 20% and a cumulative mass volume error of less than 1%.

Although the present invention has been described in detail with regard to the preferred embodiment thereof, one skilled in the art will easily realize that other versions are possible, and that the invention is only intended to be limited in scope by the following claims.

The invention claimed is:

1. In a well bore operation in which a particulate is added to a fluid stream in a conduit, a method of determining the concentration of said particulate in said fluid stream comprising the steps of:
   measuring the rate of flow of said fluid stream in said conduit;
   determining the rate of particulate flow in said fluid stream using an output of an acoustic sensor operatively connected to said conduit, said output varying in response to the amount of particulate in said fluid stream and being adjusted to filter out acoustic noise unrelated to said particulate and for some or all of fluid, fluid flow, particulate, conduit and sensor characteristics;
   calculating the concentration of particulate in said fluid stream using the results from said measuring and determining steps; and
   using a digital signal processor means to produce a digital signal raw output (DSRO), said DSRO being a first digital number representative of said output from said acoustic sensor.

2. The method of claim 1 wherein said acoustic sensor is connected to said conduit at a location where said fluid stream is forced to change directions.

3. The method of claim 1 wherein said rate of particulate flow is calculated in accordance with the formula:

$$\text{Particulate Rate:} = \left[ \frac{(DSRO - \text{Amplitude Offset})}{\text{Amplitude Increment per Unit } (AIU)} \right]^{Exp}$$

where the DSRO is said first digital number representative of said output from said acoustic sensor;
where the amplitude offset is a second digital number from said digital signal processor means representative of said noise unrelated to said particulate;
wherein said amplitude increment per unit is a variable that adjusts for some or all of fluid, fluid flow, particulate, conduit and sensor characteristics; and
Exp is an exponent that adjusts for possible non-linearity in said output of said acoustic sensor.

4. The method of claim 3 wherein said particulate concentration is calculated in accordance with the formula:

$$\text{Concentration} = \frac{\text{Particulate Rate}}{\left[ \text{Clean Fluid Rate} + \frac{\text{Particulate Rate}}{\text{Particulate Density}} \right]}$$

where the particulate rate is said particulate rate from claim 3;
where the clean fluid rate is said rate of flow of said fluid stream before the addition of said particulate thereto; and
particulate density is the density of said particulate.

5. The method of claim 4 wherein said measuring is performed by a flow meter connected to said conduit to measure the rate at which said fluid is flowing through said conduit.

6. The method of claim 5 wherein said flow meter is connected to said conduit at a point before said particulate is added to said fluid stream.

7. The method of claim 5 wherein said flow meter is connected to said conduit-at a point after said particulate is added to said fluid stream.

8. The method of claim 3 wherein said particulate concentration is calculated in accordance with the formula:

$$\text{Concentration} = \frac{\text{Particulate Rate}}{\text{Slurry Flow Rate}}$$

where the particulate rate is said particulate rate from claim 3; and where said slurry flow rate is the rate of flow of said fluid when mixed with said particulate to form a slurry.

9. In a fluid conveying operation having a fluid line for carrying a fluid mixed with a particulate, an apparatus for measuring the concentration of the particulate in the fluid comprising:
- a fluid flow meter located within the fluid line for measuring the rate of flow of the fluid before or after said fluid is mixed with said particulate;
- an acoustic sensor located outside the fluid line at a bend in the fluid line for measuring the noise of particulate impacting said fluid line at said bend and producing a signal reflecting the amount of said noise;
- a calculating means for determining the concentration of the particulate using data from said fluid flow meter and said acoustic sensor; and
- a digital signal processor for producing a digital signal raw output (DSRO), said DSRO being a first digital number representative of said signal from said acoustic sensor.

10. The concentration measuring apparatus of claim 9 wherein said digital signal processor is located between said acoustic sensor and said calculating means.

11. The apparatus of claim 10 wherein said calculating means calculates said rate of particulate flow in accordance with the formula:

$$\text{Particulate Rate} = \left[\frac{(\text{Digital Signal Raw Output } (DSRO) - \text{Amplitude Offset})}{\text{Amplitude Increment per Unit } (AIU)}\right]^{Exp}$$

where the DSRO is said first digital number representative of said signal from said acoustic sensor;

where the amplitude offset is a second digital number from said digital signal processor means representative of said noise unrelated to said particulate impacting said flow line;

wherein said amplitude increment per unit is a variable that adjusts for some or all of fluid, fluid flow, particulate, fluid line and sensor characteristics; and Exp is an exponent that adjusts for possible non-linearity in said output of said acoustic sensor.

12. The apparatus of claim 11 wherein said calculating means calculates said particulate concentration in accordance with the formula:

$$\text{Concentration} = \frac{\text{Particulate Rate}}{\left[\text{Clean Fluid Rate} + \frac{\text{Particulate Rate}}{\text{Particulate Density}}\right]}$$

where the particulate rate is said particulate rate from claim 3;

where the clean fluid rate is said rate of flow of said fluid in said fluid line before the addition of said particulate thereto; and particulate density is the density of said particulate.

13. The apparatus of claim 11 wherein said particulate concentration is calculated in accordance with the formula:

$$\text{Concentration} = \frac{\text{Particulate Rate}}{\text{Slurry Flow Rate}}$$

where the particulate rate is said particulate rate from claim 11; and where said slurry flow rate is the rate of flow of said fluid in said fluid line after said fluid is mixed with said particulate.

14. In a well bore operation having a clean fluid line leading to a blender, the blender mixing a particulate with a clean fluid to create a slurry, a slurry line from said blender to a high pressure pump, the high pressure pump pumping the slurry to a wellhead using a high pressure line, a system for measuring the concentration of the particulate within the fluid comprising:
- a fluid flow meter affixed within the clean fluid line for measuring the rate of fluid flowing;
- an acoustic sensor affixed to the exterior of the high pressure line at a bend in the high pressure line, the acoustic sensor measuring acoustical noise from particulate hitting said high pressure line at said bend and producing a signal that varies in response to the amount of said noise; and
- a calculating means for calculating the concentration of said particulate in said slurry at said bend using data from said fluid flow meter and said acoustic sensor; and
- a digital signal processor for producing a digital signal raw output (DSRO), said DSRO being a first digital number representative of said signal from said acoustic sensor.

15. The concentration measuring system of claim 14 wherein said digital signal processor is located between said acoustic sensor and said calculating means.

16. The concentration measuring system of claim 15 wherein said calculating means calculates said rate of particulate flow in accordance with the formula:

$$\text{Particulate Rate} = \left[\frac{(\text{Digital Signal Raw Output } (DSRO) - \text{Amplitude Offset})}{\text{Amplitude Increment per Unit } (AIU)}\right]^{Exp}$$

where the DSRO is said first digital number representative of said signal from said acoustic sensor;

where the amplitude offset is a second digital number from said digital signal processor means representative of said noise unrelated to said particulate impacting said fluid line;

wherein said amplitude increment per unit is a variable that adjusts for some or all of fluid, fluid flow, particulate, fluid line and sensor characteristics; and Exp is an exponent that adjusts for possible non-linearity in said output of said acoustic sensor.

17. The concentration measuring system of claim 16 wherein said calculating means calculates said particulate concentration in accordance with the formula:

$$\text{Concentration} = \frac{\text{Particulate Rate}}{\left[\text{Clean Fluid Rate} + \frac{\text{Particulate Rate}}{\text{Particulate Density}}\right]}$$

where the particulate rate is said particulate rate from claim 16;

where the clean fluid rate is said rate of flow of said fluid in said fluid line before the addition of said particulate thereto; and particulate density is the density of said particulate.

18. The concentration measuring system of claim 16 wherein said particulate concentration is calculated in accordance with the formula:

$$\text{Concentration} = \frac{\text{Particulate Rate}}{\text{Slurry Flow Rate}}$$

where the particulate rate is said particulate rate from claim 11; and where said slurry flow rate is the rate of flow of said fluid in said fluid line after said fluid is mixed with said particulate.

* * * * *

UNITED STATES PATENT AND TRADEMARK OFFICE
CERTIFICATE OF CORRECTION

PATENT NO. : 7,069,776 B2
APPLICATION NO. : 10/616142
DATED : July 4, 2006
INVENTOR(S) : Robin Tudor It is certified that error appears in the above-identified patent and that said Letters Patent is hereby corrected as shown below:

On Title Page, Item (30) Foreign Application Priority Data, "2,3920,737" should read --2,392,737--.
Column 2, line 12, after "sensors", insert -- is cost--
Column 3, line 63, "pumper" should read --pump--.
Column 4, line 18, after "90°", insert --bend--.
Column 6, line 49, after "units", insert --of mass--.
Column 9, line 55, "3" should read --11--.
Column 10, line 20, delete "and".

Signed and Sealed this

Twenty-sixth Day of December, 2006

JON W. DUDAS
*Director of the United States Patent and Trademark Office*